United States Patent [19]

Casagrande et al.

[11] Patent Number: 5,144,059

[45] Date of Patent: Sep. 1, 1992

[54] CATECHOLAMINE ESTERS

[75] Inventors: Cesare Casagrande, Arese; Francesco Santangelo, Milan, both of Italy

[73] Assignee: Simes Societa Italiana Medicinali E. Sintetici S.A., Vicenza, Italy

[21] Appl. No.: 512,212

[22] Filed: Apr. 20, 1990

[30] Foreign Application Priority Data

Apr. 20, 1989 [IT] Italy ............................ 20208 A/89

[51] Int. Cl.$^5$ .............................................. C07L 69/76
[52] U.S. Cl. .................................. 560/109; 560/144; 560/157; 560/158; 560/163; 560/14; 560/12; 560/142
[58] Field of Search ............... 560/109, 142, 144, 157, 560/158, 163, 12, 14; 514/133, 532

[56] References Cited

U.S. PATENT DOCUMENTS

| | | | |
|---|---|---|---|
| 4,035,405 | 7/1977 | Bodor | 260/479 R |
| 4,138,581 | 2/1979 | Minatoya et al. | 560/109 |

FOREIGN PATENT DOCUMENTS

| | | |
|---|---|---|
| 2015573 | 10/1970 | Fed. Rep. of Germany . |
| 2117954 | 7/1972 | France . |
| 2123826 | 2/1984 | United Kingdom . |

OTHER PUBLICATIONS

Casagrande, *Angheim-Forsch/Drug Res.* 36(I), Na. 2a, 291-303, 1986.

Redell, *Chem. Abstr.*, vol. 100, No. 13, p. 13, Abstract 96090M, Mar. 26, 1984.

*Primary Examiner*—Paul J. Killos
*Attorney, Agent, or Firm*—Fleit, Jacobson, Cohn, Price, Holman & Stern

[57] ABSTRACT

The compound of the formula

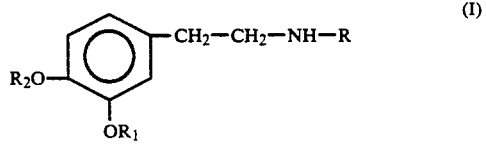

(I)

(wherein R, $R_1$ and $R_2$ have the meanings given in the description), salts thereof with pharmaceutically acceptable organic or inorganic acids, process and intermediates for the preparation thereof and a pharmaceutical composition containing said compound are described.

The compounds of formula I and the salts thereof are useful in the treatment of heart and renal diseases.

12 Claims, No Drawings

CATECHOLAMINE ESTERS

DESCRIPTION

The present invention relates to dopamine and epinine esters, to salts thereof with pharmaceutically acceptable organic or inorganic acids, to a process and intermediates for the preparation thereof and to pharmaceutical compositions containing them.

A first object of the present invention is to provide a compound of the formula

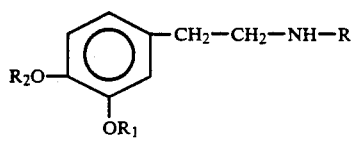

wherein
R is hydrogen or methyl;
$R_1$ and $R_2$, different from each other, are a group $R_3CO$ wherein $R_3$ is
- a $C_1$-$C_{10}$ straight or branched alkyl,
- phenyl optionally substituted by one or two substituents selected from $C_1$-$C_3$ alkyl, $C_1$-$C_3$ alkoxycarbonyl, $C_1$-$C_3$ alkylcarbonyloxy, $C_1$-$C_3$ alkylcarbonyl and halogens, or
- a group —$NR_4R_5$ wherein $R_4$ and $R_5$, which may be the same or different, are hydrogen, $C_1$-$C_{10}$ alkyl or phenyl optionally substituted by one or two substituents selected from $C_1$-$C_3$ alkyl, $C_1$-$C_3$ alkoxy, $C_1$-$C_3$ alkoxycarbonyl, $C_1$-$C_3$ alkylcarbonyloxy, $C_1$-$C_3$ alkylcarbonyl and halogens, or $R_4$ and $R_5$, together, are a polymethylene chain having from 4 to 7 carbon atoms; or, one from $R_1$ and $R_2$ has the above mentioned meanings and the second one is a group $R_4R_5$—N—$SO_2$ wherein $R_4$ and $R_5$ have the above mentioned meaning; and the salts thereof with organic or inorganic pharmaceutically acceptable acids.

The compounds of the present invention are useful in the treatment of cardiovascular and renal deseases.

Preferred meanings of $R_3$ according to this invention are methyl, ethyl, isopropyl, isobutyryl, phenyl and 4-methylphenyl.

Preferred meanings of $R_4$ and $R_5$ are methyl or ethyl.

A further object of this invention is to provide a process for the preparation of a compound of formula I and the salts thereof, comprising
(i) reducing a compound of the formula

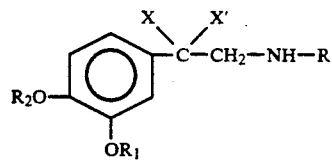

optionally protected at the amino group, wherein R has the above mentioned meaning, X and X', together, are an oxygen atom, or X' is H and X is halogen (bromine or chlorine) or hydroxy, and
(ii) removing the protective group, if any, from the amino group to yield a compound of formula I, and
(iii) if desired, adding a pharmaceutically acceptable organic or inorganic acid to a compound of formula I to yield the corresponding salt.

The process of this invention is accomplished according to conventional techniques. For example, when X and X', together, are an oxygen atom, step (i) is preferably performed by catalytic hydrogenation or by treatment with hydrides, such as triethyl silyl hydride. When X' is hydrogen and X is halogen, the latter is removed by conventional hydrogenolysis When X and X', together, are an oxygen atom, the preparation of a compound of formula II is preferably carried out from adrenalone (Merck Index 10th Edition, page 26, N° 158) or noradrenalone according to the following scheme.

Scheme 1

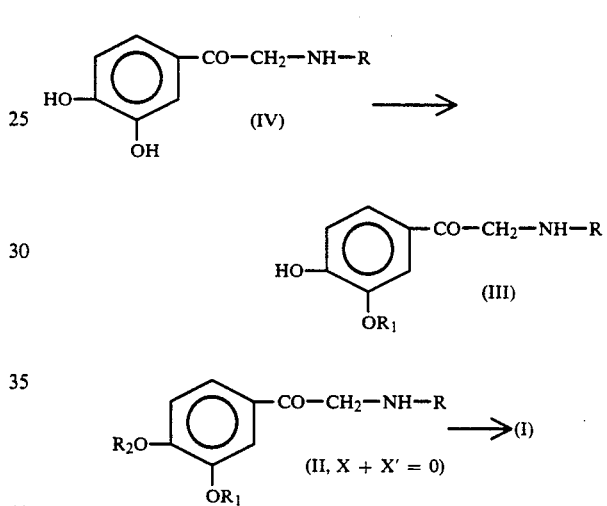

wherein R, $R_1$ and $R_2$ have the above mentioned meanings.

The compound of formula IV undergoes a first monoesterification at the hydroxy group on position 3 to yield a monoester of formula III.

The monoester III is then further esterified at the free hydroxy group on position 4 by treatment with strong base, such as sodium hydride or sodium or potassium alcoholates.

The esterification reactions are performed using reactive derivatives of carboxylic, carbamic or sulfamic acids, in an inert organic solvent at a temperature of from 0° C. to the reflux temperature of the reaction mixture.

Typical examples of reactive derivatives are carboxylic, carbamic or sulfamic acid halides, preferably chlorides.

Suitable solvents are hydrocarbons, halocarbons, ethers, esters, amides, tertiary or heterocylic amines; specific examples are methylene chloride, dioxane, ethyl acetate, dimethylformamide and pyridine.

In turn, when X is halogen or hydroxy and X' is H, the compound of formula II is preferably prepared according to scheme 2.

Scheme 2

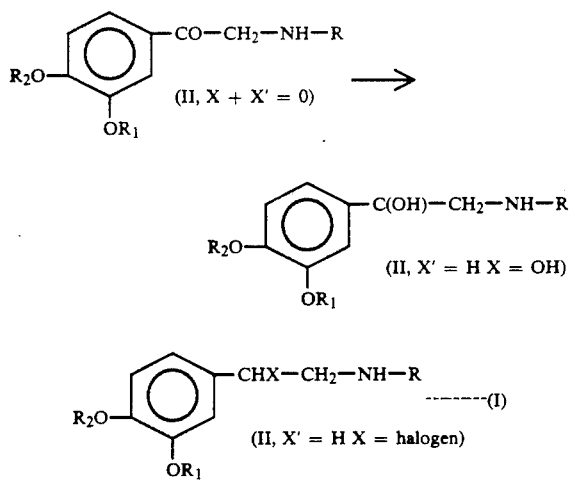

wherein R, R₁ and R₂ have the above mentioned meanings and X is preferably chlorine or bromine.

The compound of formula II (wherein X and X', together, is an oxygen atom) prepared according to scheme 1, is reduced according to conventional techniques, such as catalytic hydrogenation or reduction with sodium boron hydride or lithium boron hydride, to the corresponding aminoalcohol of formula II (wherein X' is H and X is OH) that may then be converted into the corresponding haloderivative of formula II (wherein X' is hydrogen and X is halogen) by treatment with a halogenating agent, such as, for example, thionyl chloride and boron tribromide.

It will be apparent to the artisan that the process for preparing the compounds of formula I may optionally comprise the protection of the amino group of the starting compounds of formula IV.

The protection reaction is carried out according to known techniques, preferably using benzyloxycarbonyl or t.butoxycarbonyl as protective group.

The subsequent removal of the protective group may be performed according to conventional techniques after the esterification reactions to give a compounds of formula II or after the reduction step (i) to give a compound of formula I.

Alternatively, both the deprotection of the amino group and the reduction of the carbonyl group of the compound of formula II wherein X and X', together, are an oxygen atom) or the removal of the halogen atom from the compound of formula II wherein X is halogen and X' is hydrogen) may be performed in a single step by catalytic hydrogenation.

Step (iii) is carried out according to conventional techniques.

Preferably, the pharmaceutically acceptable acid is added to the reaction mixture in step (i) or (ii), thus obtaining the desired compound as a salt.

Examples of suitable pharmaceutically acceptable acids are hydrochloric, hydrobromic, methanesulfonic, citric and tartaric acid.

Some compounds of formula II are novel.

It is therefore another object of this invention to provide the compounds of formula

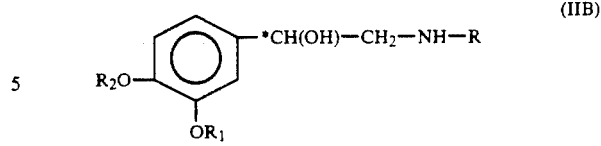

wherein
the asterisk identifies an asymmetric carbon atom,
R is hydrogen or methyl;
one from $R_1$ and $R_2$ is a group $R_3CO$ wherein $R_3$ is a group $-NR_4R_5$ wherein $R_4$ and $R_5$, which may be the same or different, are hydrogen, $C_1$-$C_{10}$ alkyl or phenyl optionally substituted by one or two substituents selected from $C_1$-$C_3$ alkyl, $C_1$-$C_3$ alkoxy, $C_1$-$C_3$ alkoxycarbonyl, $C_1$-$C_3$ alkylcarbonyloxy, $C_1$-$C_3$ alkylcarbonyl and halogens, or $R_4$ and $R_5$, together, are a polymethylene chain having from 4 to 7 carbon atoms; and
the remaining substituent from $R_1$ and $R_2$ is a group $R_3CO$ wherein $R_3$ is a $C_1$-$C_{10}$ straight or branched alkyl, or a phenyl optionally substituted by one or two substituents selected from $C_1$-$C_3$ alkyl, $C_1$-$C_3$ alkoxy, $C_1$-$C_3$ alkoxylcarbonyl and halogens,
and the salts thereof with organic or inorganic pharmaceutically acceptable acids.

Preferred meanings of $R_4$ and $R_5$ in the compounds of formula IIB are hydrogen, methyl and ethyl.

The compounds of formula IIB have an asymmetric carbon atom and may therefore be in the form of single stereoisomers or of a racemic mixture. All these forms are an object of this invention. Their preparation may be accomplished by conventional techniques, such as separation from the racemic mixture by crystallization or chromathography. Alternatively, the desired stereoisomer may be prepared by stereoselective reduction with chiral hydrides, chiral catalysts or biotechnological processes.

A further object of this invention is to provide a process for the preparation of a compound of formula (IIB) comprising
(i) reducing a compound of the formula

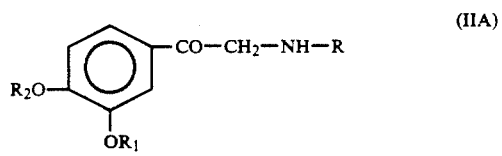

wherein
R, R1 and R2 have the meanings mentioned in relation to formula IIB, with a suitable reducing agent to afford a compound of formula IIB,
(ii) optionally resolving the racemic mixture, if any, and
(iii) if desired, adding an organic or inorganic acid to a compound of formula IIB to yield the corresponding salt.

The above process may be carried out according to conventional techniques. Step (i) is preferably accomplished by catalytic hydrogenation, or with a suitable reducing agent, such as sodium or lithium boron hydride.

The compounds of formula I are useful in therapy in the treatment of heart failure, renal failure, hypertension, pathological syndromes characterized by water or salt retention or pathological syndromes characteristic of the insufficient perfusion of vital organs.

The compounds of the present invention exert a vasodilating action on the renal district and a positive inotropic effect, producing a dose-depending increase of dP/dt (i.e. derivative of left ventricle pressure) at a dose of 1–100 mg/kg i.p., in the anesthetized dog.

Mongrels of both sexes anesthetized with sodium pentobarbital (35 mg/kg e.v.) were used. Artificial respiration was accomplished by means of an endotracheal tube with a Starling Ideal pump at a ventilation frequency of 16–18 cycles/minute, a flow rate of 16–17 ml/kg in order to obtain $pO_2$, $pCO_2$ and pH values of arterial blood of 85–100 mmHg, 30–40 mmHg and 7.35–7.45, respectively (Radiometer Copenhagen BMS 3MK 2 Blood Microsystem Blood Gas Analyzer). Duodenum was insulated by abdomen incision and a polyethylene catheter was inserted for administering the medicament. Left renal artery was isolated retroperitoneally; an electromagnetic transducer and a pneumatic obturator were positioned around the vessel to measure the blood flow and the mechanical zero, respectively.

Myocardium contractility was evaluated as the first derivative LVdP/dt of the left ventricle pressure (LVP) measured by means of a polyethylene catheter inserted into the left ventricle through the left carotid artery.

Emodynamic parameters were recorded on a Gould Brush MK 200 Graph Recorder while the pressure catheters were connected to a Bell and Howell Pressure Transducers and the electromagnetic flow transducer was connected to a Biotronex BL 613 Flowmeter.

The compounds of formula I are endowed with a greater bioavailability and a longer lasting action than dopamine and epinine and can thus also be administered orally.

Therefore, it is a further object of the present invention to provide a pharmaceutical composition containing a therapeutically effective amount of a compound of formula I or a pharmaceutically acceptable acid addition salt thereof, together with one or more excipients suitable for pharmaceutical use. The pharmaceutical compositions of the present invention may be formulated as solid preparations, such as tablets, pills, capsules, powders, pellets and suppositories, or as liquid preparations, such as suspensions, emulsions and solutions possibly to be prepared just before their use, or semi-solid preparations, such as creams, ointments and liniments.

They may also be formulated as pharmaceutical forms having a controlled or delayed release. All these formulations are prepared in conventional ways.

Moreover, other compatible active ingredients which have a complementary therapeutic action may be incorporated in the formulations.

Furthermore, it has been found that the compounds of formula IIB are useful in the ophthalmological field in conjuctival hyperemia, in controlling local hemorrhages, in the regulation of ocular pressure in glaucoma and in patients suffering from ocular hyperpression, and as a mydriatic.

It is therefore a further object of this invention to provide a composition for use in ophthalmology that contains a therapeutically or diagnostically effective amount of a compound of formula IIB or a pharmaceutically acceptable acid addition salt thereof, together with one or more pharmaceutical exipients.

Said compositions are preferably liquid, such as solutions, or semiliquid, such as creams. A solution according to this invention will preferably contain from 0.01% to 1% of a compound of formula IIB or the equivalent amount of an acid addition salt thereof. The daily dosage will vary depending on selected use and the individual response of the patient but usually it will be in the range from 0.1 to 1 mg in one or repeated administrations.

The following examples are now provided in order to disclose the present invention better.

EXAMPLE 1

To a suspension of NaH 60% in mineral oil (1.53 g) in anhydrous dimethylformamide (50 ml), at 0° C. and under a nitrogen atmosphere, is added a solution of alpha-(N-benzyloxycarbonyl-N-methylamino)-3,4-dihydroxyacetophenone (20 g) in dimethylformamide (50 ml).

After 15 minutes p.toluylchloride (8.5 ml) is added always at 0° C.

After 24 hrs at room temperature the solution is neutralized with acetic acid and evaporated to dryness. The residue is added to water, acidified with acetic acid and extracted with methylene chloride. The organic phase is dried over sodium sulphate and the solvent is evaporated.

The crude product is purified by silica gel column chromatography (eluent, methylene chloride) yielding alpha-(N-benzyloxycarbonyl-N-methylamino)-3-(4-methylbenzoyloxy)-4-hydroxyacetophenone.

m.p. 128°–134° C. (from ethyl acetate/ethyl ether)

Working in a similar manner, the following compounds were prepared:

alpha-(N-benzyloxycarbonyl-N-methylamine)-3-isobutyryloxy-4-hydroxyacetophenone m.p. 138°–140° C. (ethyl ether)

alpha-benzyloxycarbonylamino-3-(4-methylbenzoyloxy)-4-hydroxyacetophenone m.p. 172°–175° C. (ethyl acetate)

EXAMPLE 2

To a solution of alpha-(N-benzyloxycarbonyl-N-methylamino)-3-(4-methylbenzoyloxy)-4-hydroxyacetophenone (20 g; 46 mmoli), prepared as described in Example 1, in anhydrous dimethylformamide (200 ml) a suspension of NaH 60% in mineral oil (1.32 g) at 0° C. and under a nitrogen atmosphere is added.

After two hours at 0° C., a solution of isobutyrylchloride (5.9 g; 55 mmoles) in anhydrous dimethylformamide (10 ml) is added. After one hour, the reaction mixture is poured in iced water and repeatedly extracted with ether.

The organic extracts are combined and dried over sodium sulphate and evaporated, thus yielding alpha-(N-benzyloxycarbonyl-N-methylamino)-3-(4-methylbenzoyloxy)-4-isobutyryloxyacetophenone as an oil (thin layer chromatography: eluent, toluene:ethyl acetate=8:2; detection U.V., $I_2$ vapors).

$^1$H-NMR (60 MHz, $CDCl_3$): delta (ppm): 1.10 (6H, d); 2.45 (3H, s); 2.68 (1H, m); 3.02 (3H, s); 4.70 (2H, d); 5.20 (2H, d); 7.21–8.10 (12H, m).

Working in a similar manner, the following compounds were prepared:

alpha-(N-benzyloxycarbonyl-N-methylamino)-3-(4-methylbenzoyloxy)-4-(N,N-dimethylcarbamoyloxy)acetophenone oil, (thin layer chromatography: eluent, CH$_2$Cl$_2$:toluene:CH$_3$OH=25:5:3; detection U.V., I$_2$ vapors).

$^1$H-NMR (60 MHz, CDCl$_3$): delta (ppm): 2.46 (3H, s); 2.88 (6H, s); 3.06 (3H, s); 4.73 (2H, d); 5.20 (2H, d); 7.30–8.23 (12H, m).

alpha-(N-benzyloxycarbonyl-N-methylamino)-3-isobutyryloxy-4-(4-methylbenzoyloxy)acetophenone
    m.p. 102°–104° C. (ethyl ether/petroleum ether).

alpha-benzyloxycarbonylamino-3-(4-methylbenzoyloxy)-4-(N,N-dimethylcarbamoyloxy)acetophenone
    m.p. 147°–148° C. (ethyl ether).

alpha-benzyloxycarbonylamino-3-(4-methylbenzoyloxy)-4-(isobutyryloxy)acetophenone oil (thin layer chromatography: eluent, CH$_2$Cl$_2$:ethyl acetate=9:1; detection U.V. light, I$_2$ vapors)

$^1$H-NMR (60 MHz, CDCl$_3$): delta (ppm): 1.15 (6H, d); 2.46 (3H, s); 4.71 (2H, d); 5.25 (2H, s); 7.20–8.23 (12H, m).

alpha-(N-benzyloxycarbonyl-N-methylamino)-3-isobutyryloxy-4-(N-methylcarbamoyloxy)acetophenone
    oil; in this case, it has not been necessary to use NaH as a base (thin layer chromatography: eluent, toluene:ethyl acetate 8:2, or CH$_2$Cl$_2$:toluene:CH$_3$OH=25:5:3; detection U.V., I$_2$ vapors).

Mass spectrum (chemical ionization, positive ions, ionization gas:isobutane) m/e 443 (M$^+$ + 1).

alpha-(N-benzyloxycarbonyl-N-methylamino)-3-isobutyryloxy-4-(N,N-dimethylsulfamoyloxy)acetophenone
    oil, (thin layer chromatography: eluent, CH$_2$Cl$_2$:CH$_3$OH=98:2; detection U.V., I$_2$ vapors).

Mass spectrum (chemical ionization, positive ions, ionization gas:ammonia) m/e 493 (M$^+$ + 1).

alpha-(N-benzyloxycarbonyl-N-methylamino)-3-isobutyryloxy-4-(4-methoxycarbonylbenzoyloxy)acetophenone
    m.p. 88°–89° C. (ethyl ether/petroleum ether).

alpha-(N-benzyloxycarbonyl-N-methylamino)-3-isobutyryloxy-4-(4-isobutyryloxybenzoyl)acetophenone
    oil, (thin layer chromatography: eluent, toluene:ethyl acetate=7:3; detection U.V., I$_2$ vapors).

Mass spectrum (chemical ionization, positive ions, ionization gas:ammonia) m/e 473 (M$^+$ +18), 456 M$^+$ +1).

EXAMPLE 3

To a solution of alfa-(N-benzyloxycarbonyl-N-methylamino)-3-(4-methylbenzoyloxy)-4-isobutyryloxy-acetophenone (23.2 g; 46.87 mmoles), prepared as described in Example 2, in methanol (230 ml) at 0°–5° C., sodium boron hydride (1.74 g; 45.99 mmoles) is added.

After 45 minutes the solution is acidified with hydrochloric acid, concentrated to small volume, diluted with methylene chloride and washed with water.

After drying over sodium sulphate, the solvent is evaporated yielding 3-O-(4-methylbenzoyl)-4-O-isobutyryl-N-benzyloxycarbonyladrenaline as an oil (thin layer chromatography; eluent, toluene:ethyl acetate=7:3; detection U.V. light, I$_2$ vapors)

$^1$H-NMR (60 MHz, CDCL$_3$): delta (ppm): 1.06 (6H, d); 2.40 (3H, s); 2.63 (1H, m); 2.83 (3H, s); 3.50 (2H, d); 4.91 (1H, t); 5.08 (2H, s); 7.16–7.33 (10H, m); 8.06 (2H, d).

Working in a similar manner, the following compounds were prepared:

3-O-(4-methylbenzoyl)-4-O-(N,N-dimethylcarbamoyl)-N-benzyloxycarbonyladrenaline
    oil (thin layer chromatography; eluent, toluene:ethyl acetate=1:1; detection U.V. light, I$_2$ vapors)

$^1$H-NMR (60 MHz, CDCl$_3$): delta (ppm): 2.48 (3H, s); 2.86 (6H, s); 2.95 (3H, s); 3.53 (2H, d); 5.03 (1H, m); 5.23 (2H, s); 7.25–7.40 (10H, m); 8.06 (2H, d).

3-O-isobutyryl-4-O-(4-methylbenzoyl)-N-benzyloxycarbonyladrenaline
    oil (thin layer chromatography; eluent, toluene:ethyl acetate=7:3; detection U.V. light, I$_2$ vapors)

$^1$H-NMR (60 MHz, CDCl$_3$): delta (ppm): 1.10 (3H, d); 2.56 (3H, s); 2.66 (1H, m); 2.98 (3H, s); 3.50 (2H, d); 5.00 (1H, m); 5.18 (2H, s); 7.23–7.36 (10H, m); 8.08 (2H, d).

3-O-(4-methylbenzoyl)-4-O-isobutyryl-N-benzyloxycarbonylnoradrenaline
    oil (thin layer chromatography; eluent CH$_2$Cl$_2$:ethyl acetate=9:1; detection U.V. light, I$_2$ vapors)

$^1$H-NMR (60 MHz, CDCl$_3$): delta (ppm): 1.10 (6H, d); 2.43 (3H, s); 2.70 (1H, m); 3.40 (2H, m); 4.85 (1H, m); 5.13 (2H, s); 7.18–7.38 (10H, m); 8.13 (2H, m).

3-O-(4-methylbenzoyl)-4-O-(N,N-dimethylcarbamoyl)-N-benzyloxycarbonylnoradrenaline
    oil (thin layer chromatography, eluent, toluene:methanol=95:5; detection U.V. light, I$_2$ vapors)

$^1$H-NMR (60 MHz, CDCl$_3$): delta (ppm): 2.41 (3H, s); 2.85 (6H, s); 3.39 (2H, d); 4.78 (1H, m); 5.16 (2H, s); 7.26–7.43 (10H, m); 8.16 (2H, d).

3-O-isobutyryl-4-O-(4-methylcarbamoyl)-N-benzyloxycarbonyladrenaline
    oil (thin layer chromatography; eluent, CH$_2$Cl$_2$:toluene:CH$_3$OH=25:5:4; detection U.V. light, I$_2$ vapors)

Mass spectrum (chemical ionization, positive ions, ionization gas:isobutane) m/e 445 (M$^+$ + 1).

3-O-isobutyryl-4-O-(N,N-dimethylsulfamoyl)-N-benzyloxycarbonyladrenaline
    oil (thin layer chromatography; eluent, CH$_2$Cl$_2$:toluene:CH$_3$OH=25:5:2; detection U.V. light, I$_2$ vapors)

Mass spectrum (chemical ionization, positive ions, ionization gas:ammonia) m/e 495 (M$^+$ + 1).

3-O-isobutyryl-4-O-(4-methoxycarbonylbenzoyl)-N-benzyloxycarbonyladrenaline
    oil (thin layer chromatography; eluent, CH$_2$Cl$_2$:toluene:CH$_3$OH=25:5:2; detection U.V. light, I$_2$ vapors)

Mass spectrum (chemical ionization, positive ions, ionization gas:ammonia) m/e 550 (M$^+$ + 1).

3-O-isobutyryl-4-O-(4-isobutyryloxybenzoyl)-N-benzyloxycarbonyladrenaline
    oil (thin layer chromatography; eluent, CH$_2$Cl$_2$:toluene:CH$_3$OH=25:5:3; detection U.V. light, I$_2$ vapors)

Mass spectrum (chemical ionization, positive ions, ionization gas:ammonia) m/e 578 (M$^+$ + 1).

EXAMPLE 4

10% palladium on charcoal (2.4 g) was added to a solution of 3-O-(4-methylbenzoyl)-4-O-isobutyryl-N-benzyloxycarbonyladrenaline (12 g; 23.74 mmoles), prepared as described in Example 3, in acetic acid (100 ml) and HCl 37% in ethanol (3.5 ml).

The suspension is hydrogenated at room temperature at a hydrogen pressure of 2–3 atmospheres. After theoretical adsorption of hydrogen, the suspension is filtered and evaporated.

The oily residue is crystallized from ethyl ether yielding 3-O-(4-methylbenzoyl)-4-O-isobutyryl adrenaline hydrochloride, with m.p. 147°–149° C.

Working in a similar manner, the following compounds were obtained:

3-O-(4-methylbenzoyl)-4-O-(N,N-dimethylcarbamoyl)adrenaline hydrochloride chromatographically pure hygroscopic solid (thin layer chromatography; eluent, $CH_2Cl_2:CH_3OH:CH_3COOH=79:15:1$, detection $I_2$ vapors).

$^1$H-NMR (60 MHz, $CDCl_3$): delta (ppm): 2.30 (3H, s); 2.66 (9H, s); 3.08 (2H, m); 5.08 (1H, m); 7.02–7.48 (5H, m); 7.90 (2H, d).

3-O-isobutyryl-4-O-(N,N-dimethylcarbamoyl)adrenaline hydrochloride chromatographically pure hygroscopic solid (thin layer chromatography; eluent, $CH_2Cl_2:CH_3OH:H_2O:CH_3COOH=79:15:1:1$, detection $I_2$ vapors).

$^1$H-NMR (300 MHz, $D_2O$): delta (ppm): 1.27 (6H, d); 2.77 (3H, s); 2.92 (1H, sextet); 2.96 (3H, s); 3.08 (3H, s); 3.24–3.38 (2H, m); 5.08–5.13 (1H, 2d); 7.30–7.42 (3H, m).

3-O-isobutyryl-4-O-(4-methylbenzoyl)adrenaline hydrochloride m.p. 141°–144° C. (from ethyl ether)

3-O-(4-methylbenzoyl)-4-O-isobutyryl-noradrenaline hydrochloride chromatographically pure oil (thin layer chromatography, eluent $CH_2Cl_2:CH_3OH:CH_3COOH=79:15:1$; detection $I_2$ vapors).

$^1$H-NMR (60 MHz, DMSO-$d_6$): delta (ppm): 1.06 (6H, d); 2.46 (3H, s); 3.13 (2H, m); 5.08 (1H, m); 7.38–7.56 (5H, m); 8.13 (2H, m).

3-O-(4-methylbenzoyl)-4-O-(N,N-dimethylcarbonyl)-noradrenaline hydrochloride chromatographically pure oil (thin layer chromatography, eluent $CH_2Cl_2:CH_3OH:CH_3COOH=79:15:1$; detection $I_2$ vapors).

$^1$H-NMR (60 MHz, DMSO-$d_6$): delta (ppm): 2.48 (3H, s); 2.82 (6H, s); 3.02 (2H, m); 5.06 (1H, m); 7.28–8.20 (7H, m).

3-O-isobutyryl-4-O-(4-methylcarbamoyl)adrenaline hydrochloride oil (thin layer chromatography; eluent, methylene chloride:methyl alcohol:water:acetic acid=79:15:1:1; detection $I_2$ vapours)

Mass spectrum (chemical ionization, positive ions, ionization gas:isobutane) m/e 311 ($M^+$ +1)

$^1$H-NMR (300 MHz, $D_2O$) delta (ppm): 1.28 (6H, d); 2.76 (6H, s), 2.9 (1H, m), 3.24–3.38 (2H, m), 5.01 (1H, dd), 7.30–7.42 (3H, m).

3-O-isobutyryl-4-O-(N,N-dimethylsulfamoyl)-adrenaline hydrochloride m.p. 155°–157° C. (ethyl alcohol)

3-O-isobutyryl-4-O-(4-methoxycarbonylbenzoyl)-adrenaline hydrochloride m.p. 167°–171° C. (ethyl acetate)

3-O-isobutyryl-4-O-(4-isobutyryloxybenzoyl)-adrenaline hydrochloride m.p. 145°–150° C. (methylene chloride/ethyl ether)

EXAMPLE 5

Thionyl chloride (4.66 g; 39.17 mmoles) is added to a solution of 3-O-(4-methylbenzoyl)-4-O-isobutyryladrenaline hydrochloride (4 g; 7.38 mmoles), prepared as described in Example 4, in anhydrous methylene chloride (40 ml), kept at 0° C. under nitrogen atmosphere.

After one hour at room temperature the solution is evaporated. The residue is crystallized from ethyl ether/ethyl acetate yielding 2-chloro-2-[3-(4-methylbenzoyloxy)-4-isobutyryloxyphenyl]-N-methyl-ethylamine hydrochloride, m.p. 182°–184° C.

Working in a similar manner, the following compounds are obtained:

2-chloro-2-[3-(4-methylbenzoyloxy)-4-(N,N-dimethylcarbamoyloxy)-phenyl]-N-methyl-ethylamine hydrochloride m.p. 170°–173° C. (ethyl acetate/ethyl ether)

2-chloro-2-[3-isobutyryloxy-4-(4-methylbenzoyloxy)-phenyl]-N-methyl-ethylamine hydrochloride m.p. 172°–175° C. (ethyl ether)

2-chloro-2-[3-(4-methylbenzoyloxy)-4-isobutyryloxyphenyl]ethyl-amine hydrochloride chromatographically pure oil (thin layer chromatography; eluent, $CH_2Cl_2:CH_3OH:CH_3COOH=79:15:1$; detection, $I_2$ vapors).

$^1$H-NMR (60 MHz, DMSO-$d_6$): delta (ppm): 1.05 (6H, d); 2.50 (3H, s); 3.56 (2H, m); 5.68 (1H, m); 7.33–8.15 (7H, m).

2-chloro-2-[3-(4-methylbenzoyloxy)-4-(N,N-dimethylcarbamoyloxy)-phenyl]ethylamine hydrochloride chromatographically pure oil (thin layer chromatography; eluent, $CH_2Cl_2:CH_3OH:CH_3COOH=79:15:1$; detection, U.V. light, $I_2$ vapors).

$^1$H-NMR (60 MHz, DMSO-$d_6$): delta (ppm): 2.46 (3H, s); 2.84 (6H, s); 3.56 (2H, d); 5.66 (1H, t); 7.40–8.30 (7H, m).

2-chloro-2-[3-isobutyryloxy-4-(N-methylcarbamoyloxy)-phenyl]ethylamine hydrochloride m.p. 138°–139° C. (ethyl acetate)

2-chloro-2-[3-isobutyryloxy-4-(N,N-dimethylsulfamoyloxy)-phenyl]-ethylamine hydrochloride m.p. 156°–158° C. (ethyl ether)

2-chloro-2-[3-isobutyryloxy-4-(4-methoxycarbonylbenzoyloxy)phenyl]-ethylamine hydrochloride m.p. 145°–166° C. (slow decomposition, toluene/ethyl ether)

2-chloro-2-[3-isobutyryloxy-4-(4-isobutyryloxybenzoyloxy)phenyl]-ethylamine hydrochloride

EXAMPLE 6

10% palladium on charcoal (1 g) is added to a solution of 2-chloro-2-[3-(4-methylbenzoyloxy)-4-isobutyryloxyphenyl]-N-methyl-ethylamine hydrochloride (3.5 g; 6.67 mmoles), prepared as described in Example 5, in anhydrous dimethylformamide (35 ml).

The suspension is hydrogenated at room temperature at a hydrogen pressure of 2–3 atmospheres. After theoretical adsorption of hydrogen, the suspension is filtered and evaporated.

The residue is crystallized from ethanol/ethyl ether yielding 3-O-(4-methylbenzoyl)-4-O-isobutyryl-N-methyl-dopamine hydrochloride, m.p. 140°–141° C.

Working in a similar manner, the following compounds were prepared:

3-O-(4-methylbenzoyl)-4-O-(N,N-dimethylcarbamoyl)-N-methyl-dopamine hydrochloride m.p. 112°–114° C. (ethyl acetate)

3-O-isobutyryl-4-O-(4-methylbenzoyl)-N-methyl-dopamine hydrochloride m.p. 193°–194° C. (ethanol/ethyl ether)

bis[3-O-(4-methylbenzoyl)-4-O-isobutyryldopamine]-dibudinate m.p. 253°–254° C. (ethanol/ethyl ether)

bis[3-O-(4-methylbenzoyl)-4-O-(N,N-dimethylcarbamoyl)dopamine]dibudinate m.p. 259°-261° C. (ethyl alcohol/ethyl ether).

3-O-isobutyryl-4-O-(N-methylcarbamoyl)-N-methyl-dopamine hydrochloride m.p. 192°-195° C. (ethyl alcohol/ethyl ether)

$^1$H-NMR (300 MHz D$_2$O) delta (ppm) 1.27 (6H, d), 2.71 (3H, s), 2.78 (3H, s), 2.90 (1H, m), 3.05 (2H, t), 3.32 (2H, t), 7.13-7.29 (3H, m).

3-O-isobutyryl-4-O-(N,N-dimethylsulfamoyl)-N-methyl-dopamine hydrochloride m.p. 143°-145° C. (ethyl alcohol/ethyl ether)

$^1$H-NMR (300 MHz, D$_2$O) delta (ppm) 1.31 (6H, d), 2.72 (3H, s), 2.97 (1H, quintetto), 2.39 (6H, s), 3.06 (2H, t), 3.32 (2H, t), 7.24 (1H, d), 7.32 (1H, dd), 7.48 (1H, d)

3-O-isobutyryl-4-O-(4-methoxycarbonylbenzoyl)-N-methyl-dopamine hydrochloride m.p. 208°-211° C. (ethyl acetate)

$^1$H-NMR (300 MHz, CDCl$_3$) delta (ppm) 1.09 (6H, d), 2.65 (1H, quintetto), 2.74 (3H, s), 3.19-3.23 (4H, m), 33.95 (3H, s), 7.16-7.24 (3H, m), 8.12-8.21 (4H, m)

3-O-isobutyryl-4-O-(4-isobutyryloxybenzoyl)-N-methyl-dopamine hydrochloride m.p. 167°-170° C. (methylene chloride/ethyl ether)

$^1$H-NMR (300 MHz, CDCl$_3$) delta (ppm) 1.00 (6H, d), 1.33 (6H, d), 2.65 (1H, quintetto), 2.82 (1H, quintetto), 3.22 (4H, bs), 7.15-7.21 (5H, m) 8.15 (2H, d).

EXAMPLE 7

Permeability Rate of
3-O-(4-Methylbenzoyl)-4-O-(N,N-Dimethylcarbamoyl)adrenaline Hydrochloride (Identified as 2B223) and
3-O-Isobutyryl-4-O-(N,N-Dimethylcarbamoyl)adrenaline Hydrochloride (Identified as 2B852)

Perfusion method: pig corneas have been removed with about 2 mm of sclera and set on a perfusion cell.

The receiving compartment and that of the donor were respectively filled with 6 ml and 1 ml of GBR solution (Glutathione Bicarbonate Ringer's solution) preheated at 35° C.

During the analysis the cells were maintained at a temperature of 34°-35° C. with a thermostat (REACTI-THERM, Pierce). Besides, the solutions in the 2 compartments were maintained under a flow of 95% O$_2$—5% CO$_2$ mixture.

The GBR solution in the donor compartment was then substituted with 1 ml of GBR solution saturated with O$_2$—CO$_2$ containing, 2B223 or 2B852 (2.5 mM).

Aliquots of 600 μl were withdrawn from the receiving compartment every 40 minutes for a period of 4 hours and immediately replaced with an equal volume of GBR.

A solution of GBR with diclofenac (0.1%) maintained at the same conditions (temperature 34°-35° C. and gassed with (O$_2$—CO$_2$) acted as control aliquots from the control were withdrawn at the same times.

The samples and the controls at various times were immediately analyzed by HPLC.

Solutions: Glutathione Bicarbonate Ringer's (GBR), pH 7.65. The GBR solution was prepared in two parts: part I was composed of sodium chloride 12.4 g/l, potassium chloride 0.716 g/l, sodium dihydrogen phosphate monohydrate 0.206 g/l and sodium bicarbonate 4.908 g/l while part II was composed of calcium chloride 0.230 g/l, magnesium chloride 0.318 g/l, glucose 1.8 g/l and oxidized glutathioine 0.184 g/l. Both parts were stored cold and utilized within two weeks.

Equal volumes of part I and II were mixed prior to use.

TABLE 1

Permeability rate of 2B223 and 2B852 across excised cornea. Amounts (nMoles) of the unchanged product and of epinephrine released by 2B223 and 2B852 in the receiving compartment.

| COMPOUND | INITIAL AMOUNT IN DONOR COMPARTMENT (nMoles) | PERMEABILITY RATE (nMoles) | | | |
|---|---|---|---|---|---|
| | | 40 min. | 80 min. | 120 min. | 160 min. |
| 2B223 | 2450 | 0.0 | 1.3 | 4.1 | 23.5 |
| EPINEPHRINE | | 15.8 | 21.7 | 23.4 | 26.2 |
| 2B852 | 2770 | 0.0 | 0.0 | 0.0 | 0.0 |
| EPINEPHRINE | | 14.5 | 23.7 | 28.9 | 32.0 |

It is known that epinephrine is a drug potentially useful in ophthalmology; however, it does not permeate cornea barrier when applied topically to the eye. The above experiment shows that epinephrine is released inside the eye after topical administratio of 2B223 and 2B852.

EXAMPLE 8

Intraocular pressure in rabbit was also tested as shown in Table 2 and 3.

TABLE 2

Intraocular pressure (mm Hg) in rabbit after topical application of 0.1% solution of 2B223.

| ANIMAL | TIME (hours) | | | | |
|---|---|---|---|---|---|
| | 0 | 1 | 2 | 4 | 8 |
| animal 1 | 16 | 12 | 13 | 14 | 15 |
| animal 2 | 16 | 13 | 14 | 15 | 16 |
| animal 3 | 15 | 12 | 13 | 14 | 15 |
| animal 4 | 16 | 11 | 13 | 13 | 14 |
| animal 5 | 17 | 13 | 14 | 15 | 16 |
| animal 6 | 16 | 12 | 13 | 14 | 15 |
| N | 6 | 6 | 6 | 6 | 6 |
| MEAN | 16.0 | 12.2 | 13.3 | 14.2 | 15.2 |
| SD | 0.6 | 0.8 | 0.5 | 0.8 | 0.8 |

TABLE 3

Intraocular pressure (mm Hg) in rabbit after topical applications of 0.1% solution of 2B852.

| ANIMAL | TIME (hours) | | | | |
|---|---|---|---|---|---|
| | 0 | 1 | 2 | 4 | 8 |
| animal 1 | 15 | 12 | 13 | 14 | 16 |
| animal 2 | 16 | 13 | 14 | 15 | 15 |
| animal 3 | 16 | 12 | 14 | 14 | 16 |
| animal 4 | 16 | 11 | 13 | 14 | 16 |
| animal 5 | 15 | 11 | 13 | 14 | 14 |
| animal 6 | 16 | 12 | 14 | 15 | 15 |
| N | 6 | 6 | 6 | 6 | 6 |
| MEAN | 15.7 | 11.8 | 13.5 | 14.3 | 15.3 |
| SD | 0.5 | 0.8 | 0.6 | 0.5 | 0.8 |

EXAMPLE 8

Action of 2B223 and 2B852 on Ocular Hypertension in Man 1 drop of a 0.1% solution of 2B223 or 2B852, respectively, was instilled into each eye of 8 patients (males) suffering from non-severe ocular hypertension. Ocular pressure was tested at time 0, and 30, 120, 180 minutes after the ocular instillation. At same times blood pressure and heart rate were also tested.

The results shown in Table 4 and 5 demonstrate that the maximum action is reached after 120 minutes with both compounds.

No modification in the blood pressure and heart rate has been found. Both compounds were well tolerated locally.

TABLE 4

Ocular Pressure (mmHg) after instillation of a drop of a 0.1% solution of 2B223 in right (r.) and left (l.) eye of 4 patients.

| PATIENT | TIME (minutes) | | | | | | | |
|---|---|---|---|---|---|---|---|---|
| | 0 | | 30 | | 120 | | 180 | |
| | r. | l. | r. | l. | r. | l. | r. | l. |
| Patient 1 | 27 | 26 | 24 | 25 | 22 | 20 | 23 | 22 |
| Patient 2 | 24 | 26 | 23 | 25 | 21 | 22 | 22 | 24 |
| Patient 3 | 23 | 26 | 24 | 25 | 23 | 22 | 24 | 24 |
| Patient 4 | 27 | 25 | 25 | 23 | 23 | 22 | 24 | 25 |
| N | 4 | 4 | 4 | 4 | 4 | 4 | 4 | 4 |
| MEAN | 25.3 | 25.8 | 24.0 | 24.5 | 22.3 | 21.5 | 23.3 | 23.8 |
| SD | 2.1 | 0.5 | 0.8 | 1.0 | 1.0 | 1.0 | 1.0 | 1.3 |

TABLE 5

Ocular Pressure (mmHg) after instillation of a drop of a 0.1% solution of 2B852 in right (r.) and left (l.) eye of 4 patients.

| PATIENT | TIME (minutes) | | | | | | | |
|---|---|---|---|---|---|---|---|---|
| | 0 | | 30 | | 120 | | 180 | |
| | r. | l. | r. | l. | r. | l. | r. | l. |
| Patient 1 | 26 | 27 | 25 | 26 | 23 | 24 | 25 | 23 |
| Patient 2 | 25 | 26 | 24 | 24 | 22 | 22 | 22 | 23 |
| Patient 3 | 24 | 26 | 23 | 25 | 23 | 24 | 23 | 23 |
| Patient 4 | 28 | 27 | 26 | 26 | 24 | 25 | 24 | 25 |
| N | 4 | 4 | 4 | 4 | 4 | 4 | 4 | 4 |
| MEAN | 25.8 | 26.5 | 24.0 | 25.3 | 23.0 | 23.8 | 23.5 | 23.8 |
| SD | 1.7 | 0.6 | 0.8 | 1.0 | 0.8 | 1.3 | 1.3 | 1.0 |

We claim:

1. A compound of the formula

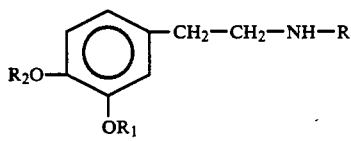

(I)

wherein
- R is hydrogen or methyl;
- $R_1$ and $R_2$, different from each other, are a group $R_3CO$ wherein $R_3$ is
  - a $C_1$-$C_{10}$ straight or branched alkyl,
  - phenyl optionally substituted by one or two substituents selected from $C_1$-$C_3$ alkyl, $C_1$-$C_3$ alkoxycarbonyl, $C_1$-$C_3$ alkylcarbonyloxy, $C_1$-$C_3$ alkylcarbonyl and halogens, or
  - a group —$NR_4R_5$ wherein $R_4$ and $R_5$, which may be the same or different, are hydrogen, $C_1$-$C_{10}$ alkyl or phenyl optionally substituted by one or two substituents selected from $C_1$-$C_3$ alkyl, $C_1$-$C_3$ alkoxy, $C_1$-$C_3$ alkoxycarbonyl, $C_1$-$C_3$ alkylcarbonyloxy, $C_1$-$C_3$ alkylcarbonyl and halogens, or $R_4$ and $R_5$, together, are a polymethylene chain having from 4 to 7 carbon atoms;
- or, one from $R_1$ and $R_2$ has the above-mentioned meanings and the second one is a group $R_4R_5$—N—$SO_2$ wherein $R_4$ and $R_5$ have the above mentioned meaning;
- or a salt thereof with an organic or inorganic pharmaceutically acceptable acid.

2. A compound according to claim 1, wherein $R_3$ is methyl, ethyl, isopropyl, isobutyryl, phenyl or 4-methylphenyl.

3. A compound according to claim 1, wherein $R_4$ and $R_5$ are methyl or ethyl.

4. A pharmaceutical composition containing a therapeutically-effective amount of a compound according to one of claims 1-3, together with one or more pharmaceutically acceptable excipients.

5. A compound of the formula

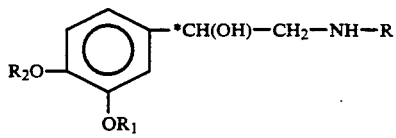

(IIB)

wherein
- the asterisk identifies an asymmetric carbon atom,
- R is hydrogen or methyl;
- one of $R_1$ and $R_2$ is a group $R_3CO$ wherein $R_3$ is a group —$NR_4R_5$ wherein $R_4$ and $R_5$, which may be the same or different, are hydrogen, $C_1$-$C_{10}$ alkyl or phenyl optionally substituted by one or two substituents selected from $C_1$-$C_3$ alkyl, $C_1$-$C_3$ alkoxy, $C_1$-$C_3$ alkoxycarbonyl, $C_1$-$C_3$ alkylcarbonyloxy, $C_1$-$C_3$ alkylcarbonyl and halogens, or $R_4$ and $R_5$, together, are a polymethylene chain having from 4 to 7 carbon atoms; and the remaining substituent from $R_1$ and $R_2$ is a group $R_3CO$ wherein $R_3$ is a $C_1$-$C_{10}$ straight or branched alkyl, or a phenyl optionally substituted by one or two substituents selected from $C_1$-$C_3$ alkyl, $C_1$-$C_3$ alkoxy, $C_1$-$C_3$ alkoxylcarbonyl and halogens, or a salt thereof with an organic or inorganic pharmaceutically-acceptable acid.

6. A compound according to claim 5, wherein $R_4$ and $R_5$ are hydrogen, methyl or ethyl.

7. A pharmaceutical composition containing a therapeutically or, a diagnostically effective amount of a compound according to one of claims 5 and 6, together with one or more pharmaceutically-acceptable excipients.

8. A compound of the formula

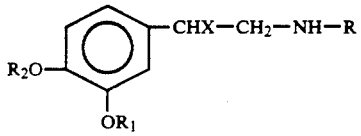 (I)

wherein
X is hydrogen (—H) or hydroxy (—OH);
R is hydrogen or methyl;
each of $R_1$ and $R_2$ is different from the other and is a group $R_3CO$—, or one of $R_1$ and $R_2$ is a group $R_3CO$— and the other is a group $R_4R_5$—N—$SO_2$;
$R_3$ is a $C_1$-$C_{10}$ straight chain or branched alkyl; phenyl; phenyl substituted by one or two substituents selected from the group consisting of $C_1$-$C_3$ alkyl, $C_1$-$C_3$ alkoxycarbonyl, $C_1$-$C_3$ alkylcarbonyloxy, $C_1$-$C_3$ alkylcarbonyl and halogen; or —$NR_4R_5$;

each of $R_4$ and $R_5$ is, independently, hydrogen; $C_1$-$C_{10}$ alkyl; phenyl; phenyl substituted by one or two substituents selected from the group consisting of $C_1$-$C_3$ alkyl, $C_1$-$C_3$ alkoxy, $C_1$-$C_3$ alkoxycarbonyl, $C_1$-$C_3$ alkylcarbonyloxy, $C_1$-$C_3$ alkylcarbonyl and halogen; or $R_4$ and $R_5$, together, are a polymethylene chain having from 4 to 7 carbon atoms;

with the proviso that, when X is —OH, each of $R_1$ and $R_2$ is a group $R_3CO$— wherein $R_3$ is —$NR_4R_5$ for one of $R_1$ and $R_2$, but not for the other; or a salt thereof with an organic or inorganic pharmaceutically-acceptable acid.

9. A compound of claim 1 wherein at least one of $R_1$ and $R_2$ is $COR_3$, wherein $R_3$ is an optionally-substituted phenyl.

10. A compound of claim 1 wherein at least one of $R_1$ and $R_2$ is $COR_3$, wherein $R_3$ is a group —$NR_4R_5$.

11. A compound of claim 1 wherein one of $R_1$ and $R_2$ is a group $R_4R_5$—$NSO_2$.

12. In a process for treating heart failure, renal failure, hypertension, pathological syndromes characterized by water or salt retention or pathological syndromes characteristic of the insufficient profusion of vital organs, which comprises administering an effective amount of an active compound to a subject in need of such treatment, the improvement wherein the active compound is a compound of claim 1.

* * * * *